May 9, 1972 F. W. ANDERSON Plant Pat. 3,157
CHERRY TREE
Filed July 20, 1970
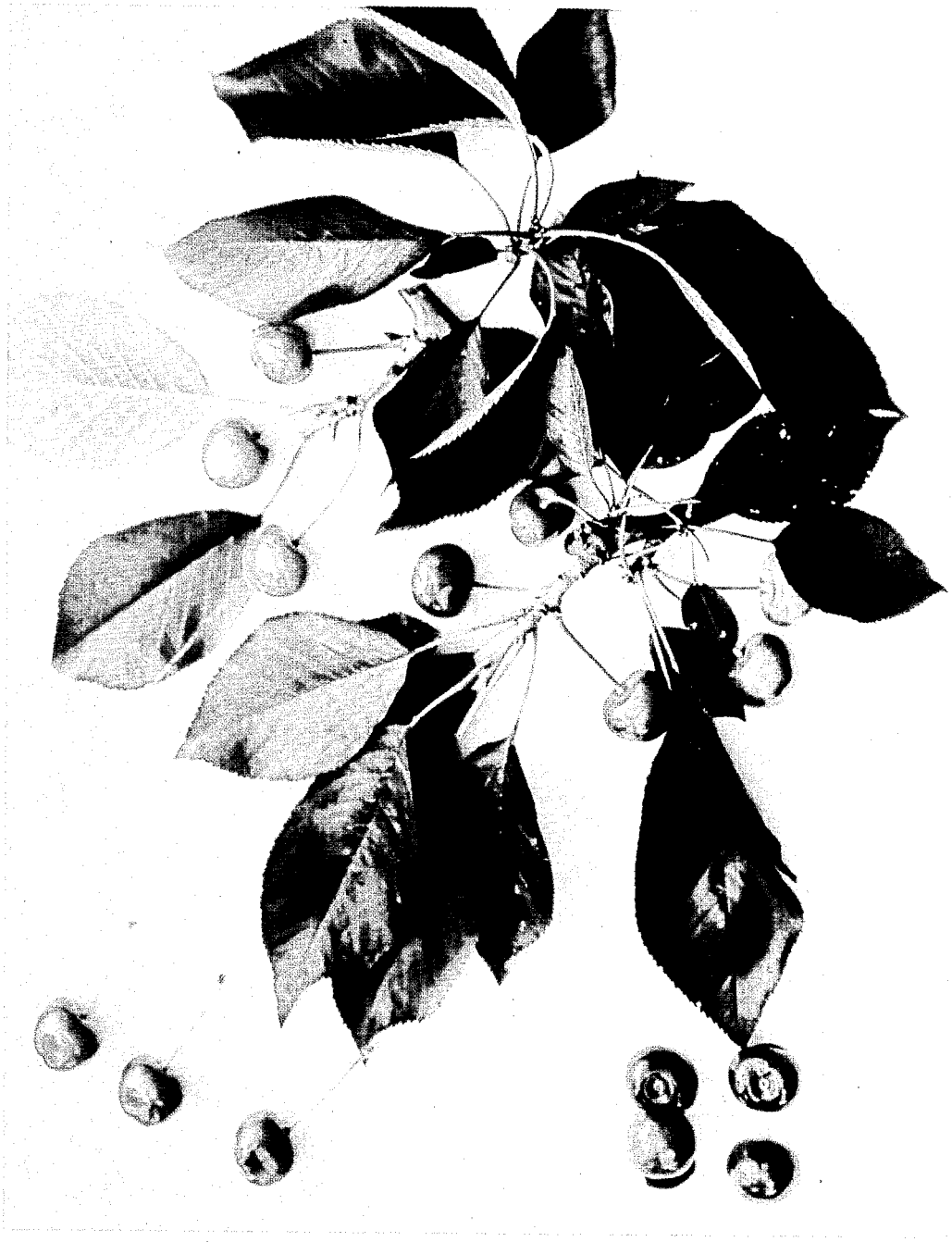
INVENTOR
Frederic W. Anderson
BY
Webster & Webster
ATTORNEYS United States Patent Office Plant Pat. 3,157
Patented May 9, 1972

3,157

CHERRY TREE

Frederic W. Anderson, Merced, Calif., assignor to Fowler Nurseries, Inc., Newcastle, Calif.

Filed July 20, 1970, Ser. No. 56,761
Int. Cl. A01h 5/03
U.S. Cl. Plt.—37 1 Claim

ABSTRACT OF THE DISCLOSURE

A dense, large size, vigorous cherry tree having an upright to spreading branching habit, foliage with large ovate leaves, white bloom of medium size, and large deep-red globose fruit, uniform in size and shape, and borne regularly and heavily; the fruit—while otherwise distinct—having general similarity to the Bing (unpatented) in size, apeparance, and harvest period.

BACKROUND OF THE VARIETY

Over a substantial number of years I have engaged in an extensive and continuing plant breeding program at my experimental nursery and orchard located near Le Grand, Merced County, Calif.; one purpose of such program being to provide imporved varieties of fruit trees. The present variety of cherry tree resulted from my endeavors in the conduct of such plant breeding program.

ORIGIN OF THE VARIETY

The herein claimed variety of cherry tree was originated by me in by experimental nursery and orchard, located as aforesaid, in the following manner:

A planting was made of a large number of seeds derived from open-pollinated flowers of the Bing, and the resultant seedings were maintained by me under careful and continuing observation; the present fruit being one of such seedlings, and which—upon bearing fruit—evidenced certain most desirable characteristics. Such one seedling was, therefore, selected by me for asexual reproduction preparatory to introduction to the trade.

ASEXUAL REPRODUCTION OF THE VARIETY

Subsequent to origination and selection by me of the present variety of cherry tree, in the manner above described, I asexually reproduced it by grafting on mature trees in my said experimental orchard, and—in maturity—such reproductions ran true to the original tree in all respects.

SUMMARY OF THE VARIETY

The herein claimed variety of cherry tree is dense, of medium size, vigorous, upright to spreading in branching habit, with large ovate leaves, white bloom of medium size, and large deep-red globose fruit which is uniform in size and shape, and borne regularly and heavily; the fruit—while having general similarity to the Bing in size, apeparance, and harvest period—being distinctively characterized, under like growing conditions, by requiring less chilling during the preceding winter, and being much more productive with fewer defective fruit, particularly doubles.

The herein claimed variety of cherry tree is further distinctively characterized by intercompatibility with the Bing Andy (United States Plant Patent No. 2,198) and likewise with the inter-sterile group of cherry trees consisting of the Bing, Lambert, and Napoleon (all unpatented).

BRIEF DESCRIPTION OF THE DRAWING

The drawing is an illustration, by photographic reproduction in color, of twigs with leaves and attached fruit, and separate fruit.

DESCRIPTION OF THE VARIETY

The botanical details of this new and distinct variety of cherry tree—with color definitions (except those in comomn color terms) referenced to Maerz and Paul Dictionary of Color—are as follows:

Tree:
- *Size.*—Large.
- *Vigor.*—Vigorous.
- *Banrching habit.*—Upright to spreading.
- *Density.*—Dense.
- *Production.*—Very productive.
- *Bearing.*—Regular bearer.

Trunk:
- *Form.*—Stocky.
- *Texture.*—Medium.

Branches:
- *Form*—stocky.
- *Lenticels.*—Number—few—size—medium.

Leaves:
- *Size.*—Large; average length (largest leaves)—7"; average width (largest leaves)—3".
- *Form.*—Ovate; acutely pointed.
- *Thickness.*—Thick.
- *Texture.*—Smooth.
- *Margin.*—Glandular; coarsely serrate.
- *Petiole.*—Medium length; medium thickness; pubescent.
- *Glands.*—Number—usually 2 on petiole; usually alternate, but occasionally opposite; medium size; reniform; red.
- *Color.*—Top side—dark green (23–A–10)—under side—lighter green (22–I–6).

Flower buds:
- *Size.*—Large.
- *Length.*—Medium.
- *Form.*—Plump.

Flowers:
- *Period of full bloom.*—Usually substantially with the Bing, but earlier after a warm winter.
- *Size.*—Medium.
- *Color.*—White.

Fruit:
- *Maturity when described.*—Hard ripe—June 7, 1970.
- *Size.*—Uniform; large; average diameter axially—1"; average transversely in suture plane—1".
- *Form.*—Uniform; symmetrical; globose; compressed laterally.
- *Defects.*—Very few doubles.
- *Suture.*—Distinct; shallow; extends from base to apex.
- *Ventral surface.*—Rounded slightly.
- *Cavity*—Rounded; shallow.
- *Base.*—Rounded.
- *Apex.*—Short; slightly depressed.

Skin:
- *Thickness.*—Medium.
- *Texture.*—Medium.
- *Tendency to crack.*—Very slight to none in normal season.
- *Down.*—Wanting.
- *Color.*—Red (6–L–6) over yellow when hard ripe; deep red (7–C–6) when full ripe.

Flesh:
- *Texture.*—Firm; fine; crisp; meaty.
- *Flavor.*—Subacid.
- *Aroma.*—Wanting.
- *Eating quality.*—Good.
- *Color.*—Deep red (7–E–6).

Stone:

*Type.*—Semifree.

*Size.* — Medium; average length — 3/8"; average breadth—5/16"; average thickness—1/4".

*Form.*—Oblong to oval.

*Tendency to split.*—None.

*Color.*—Tan (13–H–8).

Use: Market—local and long distance shipping.

Keeping quality: Good.

Shipping quality: Good.

The cherry tree and its fruit herein described may vary in slight detail due to climatic and soil conditions under which the variety may be grown; the present description being of the variety as grown in the Central Valley of California.

I claim:

1. A new and distinct variety of cherry tree, substantially as illustrated and described, which is dense, of medium size, vigorous, upright to spreading in branching habit, with large ovate leaves, white bloom of medium size, and large deep-red globose fruit, which is uniform in size and shape, and borne regularly and heavily; the fruit—while having general similarity to the Bing in size, appearance, and harvest period—being distinctively characterized in comparison by a lesser chilling requirement during the preceding winter, and by much greater production with fewer defective fruit, particularly doubles; and being further distinctively characterized by intercompatibility with the Bing Andy as well as the inter-sterile Bing, Lambert, and Napoleon.

No references cited.

ROBERT E. BAGWILL, Primary Examiner